US007016733B2

(12) United States Patent
Dublin et al.

(10) Patent No.: US 7,016,733 B2
(45) Date of Patent: Mar. 21, 2006

(54) TELEMETRY ANTENNA FOR AN IMPLANTABLE MEDICAL DEVICE

(75) Inventors: Garry L. Dublin, Maple Grove, MN (US); William D. Verhoef, Andover, MN (US); Rodney S. Wallace, Maple Grove, MN (US); Len D. Twetan, Excelsior, MN (US); Eugene Kuschnir, Forest Lake, MN (US); Gregory J. Haubrich, Champlin, MN (US); Piotr J Przybyszewski, Minneapolis, MN (US); Christine G. Kronich, St. Paul, MN (US); Eduardo H. Villaseca, deceased, late of Minneapolis, MN (US); by Bonnie Dougherty, legal representative, Briggs, PA (US)

(73) Assignee: Medtronic, Inc., Minneapolis, MN (US)

( * ) Notice: Subject to any disclaimer, the term of this patent is extended or adjusted under 35 U.S.C. 154(b) by 482 days.

(21) Appl. No.: 10/421,179

(22) Filed: Apr. 23, 2003

(65) Prior Publication Data

US 2004/0215280 A1    Oct. 28, 2004

(51) Int. Cl.
*A61N 1/365* (2006.01)
(52) U.S. Cl. .................................................... 607/36
(58) Field of Classification Search ............... 607/32, 607/36, 60; 128/903; 343/872, 873
See application file for complete search history.

(56) References Cited

U.S. PATENT DOCUMENTS

| | | | |
|---|---|---|---|
| 4,182,345 A | 1/1980 | Grose | 128/419 P |
| 4,681,111 A | 7/1987 | Silvian | 128/419 PT |
| 4,785,827 A | 11/1988 | Fischer | 128/783 |
| 5,058,581 A | 10/1991 | Silvian | 128/419 PG |
| 5,313,953 A | 5/1994 | Yomtov et al. | 128/696 |
| 5,342,408 A | 8/1994 | deCoriolis et al. | 607/32 |
| 5,470,345 A | 11/1995 | Hassler et al. | 607/36 |
| 5,562,713 A | 10/1996 | Silvian | 607/32 |
| 5,697,958 A | 12/1997 | Paul et al. | 607/31 |
| 5,730,125 A | 3/1998 | Prutchi et al. | 128/637 |
| 5,851,221 A | 12/1998 | Rieder et al. | 607/93 |
| 5,861,019 A | 1/1999 | Sun et al. | 607/60 |
| 6,167,312 A * | 12/2000 | Goedeke | 607/60 |
| 6,169,925 B1 | 1/2001 | Villaseca et al. | 607/60 |
| 6,240,317 B1 | 1/2001 | Villaseca et al. | 607/60 |
| 6,434,429 B1 | 8/2002 | Kraus et al. | 607/60 |
| 6,456,256 B1 * | 9/2002 | Amundson et al. | 343/873 |
| 6,809,701 B1 * | 10/2004 | Amundson et al. | 343/873 |
| 2002/0065539 A1 | 5/2002 | Von Arx et al. | 607/60 |
| 2002/0123776 A1 | 9/2002 | Von Arx et al. | 607/60 |
| 2003/0204216 A1 | 10/2003 | Ries et al. | 607/36 |

* cited by examiner

*Primary Examiner*—George Manuel
(74) *Attorney, Agent, or Firm*—Daniel G. Chapik; Girma Wolde-Michael (57) ABSTRACT

Improved telemetry antennas and methods of fabrication for an implantable medical device (IMD) for use in uplink telemetry (UT) and downlink telemetry (DT) transmissions between the IMD and an external medical device (EMD) are disclosed. A first telemetry antenna element is supported to extend in a first direction along a minor side of the IMD housing by a first header segment, and a second antenna element is supported to extend in a second direction along a second minor side of the IMD housing by a second header segment. The first and second antenna elements are supported to extend apart at substantially 90° to one another, i.e., substantially orthogonally, in substantially a common plane to optimize UT transmission and DT reception of UHF telemetry signals by at least one of the first and second antenna elements depending upon the mutual spatial orientation with the antenna elements of an EMD antenna.

26 Claims, 9 Drawing Sheets

TELEMETRY ANTENNA FOR AN IMPLANTABLE MEDICAL DEVICE

FIELD OF THE INVENTION

The present invention relates generally to an improved telemetry antenna and methods of fabrication for an implantable medical device (IMD) for use in uplink and downlink telemetry transmissions between the IMD and an external medical device.

BACKGROUND OF THE INVENTION

At present, a wide variety of IMDs are commercially released or proposed for clinical implantation. Such IMDs include implantable cardiac pacemakers as well as implantable cardioverter/defibrillators (ICDs) providing automatic cardioversion/defibrillation, anti-tachycardia pacing and bradycardia pacing functions of one or more heart chamber, drug delivery pumps, cardiomyostimulators, cardiac and other physiologic monitors, nerve, muscle, and muscle stimulators, e.g., sacral and spinal nerve stimulators and deep brain stimulators, cochlear implants, artificial hearts, etc.

The cardiac pacemakers, ICDs, and the various tissue, organ and nerve stimulators typically comprise an implantable pulse generator (IPG) comprising a hermetically sealed enclosure or "can" or housing and connector header combined with one or more elongated electrical medical lead coupled to the connector header. Certain implantable hemodynamic monitors also comprise a hermetically sealed enclosure or "can" or housing and connector header combined with one or more elongated electrical medical lead coupled to the connector header. Other implantable monitors comprise a hermetically sealed enclosure or "can" or housing and a sensor header that only supports a sensor, e.g., an EGM sense electrode. Such connector headers and sensor headers are formed of dielectric materials having dielectric properties. For convenience, unless specifically referred to, such dielectric connector headers and sensor headers are collectively referred to hereafter as "headers". Such hermetically sealed housings are typically formed of a conductive bio-compatible metal, although proposals have been made to form hermetically sealed housings of a non-conductive, bio-compatible polymeric or ceramic.

Such IPGs and monitors are intended to be implanted subcutaneously in a surgically prepared pocket and are designed and fabricated to be as thin and light as possible to be cosmetically unobtrusive and to avoid movement-related complications. The hermetically sealed housings and headers of such IPGs and monitors are specified as having a thickness, a height, and a width that define a displaced volume and a weight in grams. It is sought in any given design to minimize all of these specifications. The height and width are related to corresponding height and width dimensions of relatively large surface area, opposed major sides of the housing and height and width dimensions of the header. The thickness is specified to be substantially less than the height and width to facilitate implantation.

The opposed major sides can be shaped having substantially circular, oval or rectilinear outlines and can have relatively straight and curved side edge sections. The opposed major sides are typically planar and disposed substantially in parallel, although the major sides may be bowed, convex or concave or otherwise contoured to some degree to conform to a particular implantation site. The opposed major sides are typically supported and joined together at their side edges by a mutual sidewall extending between them and having a sidewall width substantially defining the thickness of the hermetically sealed housing. The mutual sidewall extends through a number of sidewall turns or corners depending on the circular, oval or rectilinear outline or combination of such outlines of the opposed major sides. Generally speaking, such housings are referred to as "prismatic".

The header is typically molded from of a relatively hard, dielectric, non-conductive polymer having a header thickness corresponding to the housing thickness and a header mounting surface that conforms to and is mechanically affixed against a mating sidewall mounting surface. The header has a header height measured in a direction extending away from the housing sidewall mounting surface and a header width measured in a direction extending along the housing header mounting surface in the width dimension of the housing. An exemplary monitor header and housing formed in this manner is disclosed in commonly assigned U.S. Pat. No. 5,851,221. An exemplary IPG header and housing formed in this manner are disclosed in commonly assigned U.S. Pat. No. 4,182,345. Other examples are found in further patents referenced herein.

The hermetically sealed housing encloses a battery providing power to electronic circuitry and associated components for providing therapies and/or monitoring and detecting conditions of the body. A sensor header supporting a sense electrode or other sensor or a connector header adapted to make connection with a proximal connector assembly of an elongated electrical medical lead or catheter is physically attached to a rectilinear housing header mounting section of the common sidewall that is typically, although no necessarily, planar and straight. One or more electrical feedthrough is mounted to the sidewall mounting surface to extend one or more feedthrough pin from the electronic circuitry into the connector header or header to make an electrical connection with one or more connector element or sensor or sense electrode supported within the connector or sensor header.

It has become common to provide a communication link between the hermetically enclosed electronic circuitry of the IMD and an external programmer or monitor or other external medical device (herein an EMD unless otherwise identified) in order to provide for downlink telemetry (DT) transmission of commands from the external device to the IMD and to allow for uplink telemetry (UT) transmission of stored information and/or sensed physiological parameters from the IMD to the EMD. As the technology has advanced, IMDs have become ever more complex in possible programmable operating modes, menus of available operating parameters, and capabilities of monitoring increasing varieties of physiologic conditions and electrical signals which place ever increasing demands on the programming system. Conventionally, the communication link between the IMD and the EMD is by encoded RF transmissions between an IMD RF telemetry antenna and transceiver and an EMD RF telemetry antenna and transceiver.

The telemetry transmission system that evolved into current common use relies upon the generation of low amplitude magnetic fields by current oscillating in an LC circuit of an RF telemetry antenna in a transmitting mode and the sensing of currents induced a closely spaced RF telemetry antenna in a receiving mode. Short duration bursts of the carrier frequency are transmitted in a variety of telemetry transmission formats. In the MEDTRONIC® product line, the RF carrier frequency is set at 175 kHz, and the RF telemetry antenna of the IPG or monitor is typically coiled wire wound about a ferrite core. The EMD is typically a programmer having a manually positioned programming head having an external RF telemetry antenna. The ferrite core, wire coil, RF telemetry antenna is not bio-compatible and can be damaged by body fluids that can penetrate the connector header, and therefore the antenna must be located inside the hermetically sealed housing. The typically conductive housing adversely attenuates the radiated RF field and limits the data transfer distance between the programmer head and the IMD RF telemetry antennas to a few inches.

The current MEDTRONIC® telemetry system employing the 175 kHz carrier frequency limits the upper data transfer rate, depending on bandwidth and the prevailing signal-to-noise ratio. Using a ferrite core, wire coil, RF telemetry antenna results in: (1) a very low radiation efficiency because of feed impedance mismatch and ohmic losses; 2) a radiation intensity attenuated proportionally to at least the fourth power of distance (in contrast to other radiation systems which have radiation intensity attenuated proportionally to square of distance); and 3) good noise immunity because of the required close distance between and coupling of the receiver and transmitter RF telemetry antenna fields.

These characteristics require that the IMD be implanted just under the patient's skin and preferably oriented with the RF telemetry antenna closest to the patient's skin. To ensure that the data transfer is reliable, it is necessary for the patient to remain still and for the medical professional to steadily hold the RF programmer head against the patient's skin over the IMD for the duration of the transmission. If the telemetry transmission takes a relatively long number of seconds, there is a chance that the programmer head will not be held steady. It is necessary to restart and repeat the uplink telemetry transmission if the uplink telemetry transmission link is interrupted by a gross movement.

In U.S. Pat. No. 4,785,827, and commonly assigned U.S. Pat. No. 5,470,345, the metal container typically used as the hermetically sealed housing of the IMD is replaced by a hermetically sealed ceramic container. The wire coil antenna is still placed inside the container, but the magnetic H field is less attenuated. It is still necessary to maintain the IMD and the external programming head in relatively close proximity to ensure that the H field coupling is maintained between the respective RF telemetry antennas.

Many proposals have been advanced for eliminating the ferrite core, wire coil, RF telemetry antenna and substituting alternative telemetry transmission systems and schemes employing far higher carrier frequencies and more complex signal coding to enhance the reliability and safety of the telemetry transmissions while increasing the data rate and allowing telemetry transmission to take place over a matter of meters rather than inches and do away with the programmer head (referred to as "far field" telemetry in certain cases). A wide variety of alternative IMD telemetry antennas mounted outside of the hermetically sealed housing within the connector header or a further header formed of a dielectric material and coupled to the telemetry transceiver within the hermetically sealed housing via a feedthrough mounted in the housing sidewall have been proposed.

In one approach, it is proposed that the elongated wire conductor of one or more electrical medical lead extending away from an IPG or monitor be employed as an RF telemetry antenna in U.S. Pat. Nos. 5,058,581 and 5,562,713 and in U.S. Patent Application Publication No. 2002/0065539, for example. A modest increase in the data transmission rate to about 8 Kb/s is alleged in the '581 and '713 patents using an RF frequency of 10–300 MHz. In these cases, the conductor wire of the medical lead can operate as a far field radiator to a more remotely located programmer RF telemetry antenna. Consequently, it is not necessary to maintain a close spacing between the EMD and IMD RF telemetry antennas or for the patient to stay as still as possible during the telemetry transmission. As noted in Publication No. 2002/0065539, the lead conductor wire can be selectively tuned in length to provide optimal theoretical frequency characteristics.

However, using the medical lead conductor as the RF telemetry antenna has several disadvantages. The radiating field is maintained by current flowing in the lead conductor, and the use of the medical lead conductor during the RF telemetry transmission may conflict with sensing and stimulation operations. RF radiation losses are high because the human body medium is lossy at higher RF frequencies. The elongated lead wire RF telemetry antenna has directional radiation nulls that depend on the direction that the medical lead extends, which varies from patient to patient. These considerations both contribute to the requirement that uplink telemetry transmission energy be set artificially high to ensure that the radiated RF energy during the RF uplink telemetry can be detected at the programmer RF telemetry antenna. Moreover, not all IMDs have lead conductor wires extending from the device.

A further U.S. Pat. No. 4,681,111 suggests the use of a stub antenna associated with the header as the IMD RF telemetry antenna for high carrier frequencies of up to 200 MHz and employing phase shift keying (PSK) modulation. The elimination of the need for a VCO and a bit rate on the order of 2–5% of the carrier frequency or 3.3–10 times the conventional bit rate are alleged. Partially shielded stub antennas for RF telemetry that project away from IMD header are disclosed in commonly assigned U.S. Pat. Nos. 6,169,925 and 6,240,317. These outwardly extending, elongated stub antennas present implantation problems since they must be extended subcutaneously for a distance away from the IMD enclosure, and share other disadvantages of use of medical electrical lead conductors as antennas.

It is proposed in commonly assigned U.S. Pat. No. 5,861,019 to form a microstrip RF telemetry antenna on or within the exterior surface of an IMD housing that is formed either of a conductive metal or of a non-conductive dielectric material. The microstrip antenna is formed of an electrically conductive radiator patch layer that is laminated upon an exterior facing side of a dielectric substrate layer of relatively constant thickness. A conductive ground plane layer is formed on the opposite side of the dielectric substrate layer to extend parallel to and at least coextensively with the radiator patch layer. The radiator patch layer is coupled to the transceiver circuitry within the IMD housing by a feedthrough extending through the dielectric substrate layer, the ground plane layer and the IMD housing side. If the IMD housing is conductive it may form the ground plane layer over which the dielectric substrate layer and the radiator patch layer are formed through deposition or other techniques. If the IMD housing is formed of a suitable non-conductive dielectric material, the ground plane layer is formed on an interior surface thereof and the radiator patch layer is formed on an exterior housing surface thereof, preferably by deposition techniques. The ground plane layer may be recessed to form a cavity backed ground plane that receives the dielectric layer and radiator patch layer within the cavity. The exterior surfaces of the radiator patch layer, the dielectric layer and any exposed surface of the ground plane layer may be electrically insulated by a radome layer which is formed of the same dielectric as the dielectric layer.

While this approach has merit, it requires complex manufacturing techniques and expense. Moreover, surgeons could mistakenly implant the IMD housing so that the microstrip antenna is disposed inward, significantly reducing the telemetry range with an external medical device.

It is generally preferable to provide an IMD RF telemetry antenna that performs as required but does not unduly increase the thickness of the IMD, the number of components that have to be implanted or assembled in use, and the cost of manufacturing. It has been proposed that one way of realizing these preferences is to support the IMD RF telemetry antenna on or within the IPG connector header.

It is suggested in U.S. Pat. Nos. 5,342,408 and 5,730,125 that an IMD RF telemetry antenna may be located in an IMD connector header and coupled to the transceiver via at least one feedthrough through the enclosure wall extending directly into the IMD connector header. Moreover, a relatively large, air core, RF telemetry antenna has been embedded into the thermoplastic connector header material of the MEDTRONIC® Prometheus programmable IPG. A proposal to place an RF telemetry antenna coil either in the IMD connector header or in a second header mounted to the hermetically sealed enclosure a distance away from the connector header is made in U.S. Pat. No. 5,313,953. Similar proposals appear in U.S. Patent Application Publication Nos. 2002/0123776 involving use of coiled wire antennas. In these approaches, attention has been directed to making the IMD RF antenna fit within the IMD existing connector header as is also suggested in further U.S. Pat. Nos. 6,434,429 and 6,470,215. Similar proposals for incorporating an EMI detecting wire strip antenna within the header are set forth in U.S. Pat. No. 5,697,958, However, it remains desirable to keep the connector header as small as possible to avoid increasing the overall dimensions and weight of the IMD that must be subcutaneously implanted. Consequently, there is little room for a wire strip or coil antenna having sufficient length to be confined within the typical header that is mounted to the sidewall of the hermetically sealed housing.

It is therefore proposed to extend the RF telemetry antenna from the header around the perimeter of the hermetically sealed enclosure in certain embodiments of the above-referenced '925 and '317 patents (see FIG. 7) and in U.S. Pat. No. 6,456,256. An elongated wire antenna is supported within an extended dielectric header spaced from the housing sidewall and extending from a feedthrough pin of an antenna feedthrough mounted in the sidewall around at least one corner of the sidewall and then through a predetermined length of the sidewall to an antenna wire free end at the termination of the extended header. The header is a connector header for an IPG or a monitor having connector elements and connector bores adapted to receive one or more electrical medical leads. The antenna feedthrough is mounted in the housing sidewall in the vicinity of the connector elements.

In the embodiment of the above-referenced '925 and '317 patents, the antenna wire extends outward away from the antenna feedthrough alongside the connector bore(s) toward the outer surface of the connector header. The antenna wire is curved to extend along the width of the connector header to a corner thereof overlying a corner of the housing sidewall and is bent to extend around the corner and along a side section of the sidewall embedded within the extended connector header. Thus, an elongated stub antenna is wrapped around the perimeter of the hermetically sealed housing in these embodiments so that it is fixed in position rather than extending freely away from the connector header within a dielectric coating as shown in other embodiments of the above-referenced '925 and '317 patents.

In the above-referenced '256 patent, the opposed major surfaces of the hermetically sealed housing have a ovaloid edges that are joined by a curved side. The antenna wire extends from the feedthrough pin supported within a similarly curved extension of the connector header extending over the curved sidewall. The curved connector header extension and curved antenna wire extend along the housing sidewall almost to the connector bore openings of the connector header.

The available space within a connector header adjacent the connector elements and the associated connector bores, feedthroughs, electrical conductors and mechanical fixing elements is relatively limited, and it is disadvantageous to locate an additional RF antenna feedthrough in proximity therewith. Accommodating the antenna feedthrough and making the electrical connection between the antenna feedthrough pin and the antenna wire when the connector header is mounted to the sidewall mounting space may be difficult in this crowded environment.

In these approaches, the conductive antenna wire is embedded within the dielectric polymer of the connector header spaced apart from the hermetically sealed sidewall, which is electrically connected to function as a grounding plane. This displacement distance between the antenna wire and the hermetically sealed grounding plane is relatively fixed through the length of the extended connector header. In the above-referenced '256, '925 and '317 patents, full advantage is not taken of the height of the connector header in the section supporting the connector elements and connector bores to displace a section of the antenna wire at a further displacement distance.

It remains desirable to provide a telemetry antenna for an IMD that eliminates drawbacks associated with the IMD telemetry antennas of he prior art. As will become apparent from the following, the present invention satisfies this need.

BRIEF SUMMARY OF THE INVENTION

In accordance with the present invention, an elongated IMD telemetry antenna is supported outside the hermetically sealed housing of an IMD having an IMD header formed of a dielectric material. A first telemetry antenna element is supported to extend in a first direction along a minor side of the IMD housing by a first header segment, and a second antenna element is supported to extend in a second direction along a second minor side of the IMD housing by a second header segment. The first and second antenna elements are supported to extend apart at substantially 90° to one another, i.e., substantially orthogonally, in substantially a common plane to optimize UT transmission and DT reception of UHF telemetry signals by at least one of the first and second antenna elements depending upon the spatial orientation of the antenna elements to an EMD antenna.

In one aspect of the invention, the wire strip fixed end is attached to an antenna feedthrough pin outer end that extends through the wall of the hermetically sealed housing at a distance from a housing corner or side junction of the first and second minor sides to an antenna feedthrough pin inner end that is coupled to transceiver circuitry within the hermetically sealed housing.

In another aspect of the invention, the elongated IMD telemetry antenna comprises an elongated wire strip extending from a wire strip fixed end to a wire strip free end and having a substantially 90° bend intermediate the wire strip fixed end and the wire strip free end. The first antenna element extends from the substantially 90° bend to the wire strip fixed end, and the second antenna element extends from the substantially 90° bend to a wire strip free end.

In a further aspect of the invention, the dielectric header material encases the first and second antenna elements to operate as a radome having a first thickness and a second thickness, respectively. The first antenna element has a first length and is supported to extend at a first side spacing from the first minor side of the hermetically sealed housing. Similarly, the second antenna element has a second length and is supported to extend at a second side spacing from the second minor side of the hermetically sealed housing.

The IMD header can comprise a connector header that includes connector bores for receiving and header connector elements for making connection with proximal lead connector elements of electrical medical leads. The header connector elements are coupled through connector feedthrough pins of connector feedthroughs mounted to a side of the hermetically sealed enclosure, the connector feedthrough pins extending into the hermetically sealed housing and coupled to electrical circuitry of the IMD. Advantageously, the antenna feedthrough is located away from these connector components, and the connector components are located between the second antenna element and the second minor side of the hermetically sealed housing to minimize interference and packaging volume.

In one preferred embodiment, the IMD connector header is formed using an undermold molded of polymeric material extending through the first and second connector header segments supporting the connector components and the telemetry antenna. The undermold assembly is affixed to the hermetically sealed housing, whereby first and second side spacings of the respective first and second antenna elements from the respective first and second minor sides are established. An overmold of dielectric material is molded over the undermold, the connector components, and the telemetry antenna to provide first and second radome thickness of dielectric material over the first and second antenna elements. Electrical connections are made between the antenna fixed end and antenna feedthrough pin and between the header connector elements and the header feedthrough pins.

In a further preferred embodiment, a pre-formed IMD connector header is initially formed of an undermold shaped to fit the second minor side and supporting the header connector elements. The undermold is affixed to the second minor side of the hermetically sealed housing, and an overmold is molded over the undermold to form a connector block of known construction and configuration having a pre-formed connector header outer surface. Electrical connections are made between the header connector elements and the header feedthrough pins. The telemetry antenna is fitted into a further molded polymer, antenna connector module that is in turn fitted against the first minor side of the hermetically sealed enclosure and the pre-formed connector header outer surface. The antenna connector module has a first segment shaped to conform to and support the first antenna element at the first side spacing from the first minor side of the hermetically sealed enclosure and a second segment shaped to conform to and support the second antenna element at the second side spacing from the second minor side of the hermetically sealed enclosure. A further overmold is molded over the telemetry antenna and the first and second segments to provide first and second radome thicknesses of dielectric material over the first and second antenna elements.

In both embodiments, the telemetry antenna feedthrough is preferably disposed into a feedthrough bore extending through a major side of the hermetically sealed housing, and the inner end of the antenna feedthrough pin is electrically coupled to transceiver circuitry disposed in close proximity thereto. The antenna feedthrough pin outer end and the telemetry antenna fixed end are welded together in a low profile weld within a weld recess formed in the housing major side. The weld site is electrically isolated from body fluids by a bio-compatible, electrically insulating material.

In relatively miniaturized IMDs, the header assembly need not be appreciably enlarged nor its volume used to support the RF telemetry antenna of the present invention comprising orthogonally disposed, first and second, IMD antenna elements. The disadvantages of employing lead conductors, if present, or using circumferentially extending or coiled wire antennas or outwardly extending stub antennas, etc., are avoided.

The orthogonally disposed, first and second, IMD telemetry antenna elements enable telemetry transmissions with orthogonally disposed EMD telemetry antennas of EMDs over distances in the range of at least two meters at a frequency of about 403 MHz with high data bit rates, low error rates and minimal power consumption.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF PREFERRED EMBODIMENTS OF THE INVENTION

The present invention relates to providing an improved RF telemetry antenna disposed outside a hermetically sealed housing of any of the IMDs of the types described above. The following description is directed to various preferred embodiments of the invention implemented in the context of an ICD IPG. However, those of skill in the art will be readily able to adapt the teachings found herein to the other IMDs listed above and others to be devised that may or may not include connector components for connecting with electrical medical leads.

In accordance with the present invention, an elongated IMD telemetry antenna is supported outside the hermetically sealed housing of an IMD by an IMD connector header that is formed to extend in first and second orthogonal directions along adjoining minor sides of the IMD housing. The IMD telemetry antenna has two primary functions: to convert the electromagnetic power of a DT transmission of an EMD telemetry antenna propagated through the atmosphere and then through body tissues into a UHF signal that can be processed by the IMD transceiver into commands and data that are intelligible to the IMD electronic operating system; and to convert the UT UHF signals of the IMD transceiver electronics into electromagnetic power propagated through the body tissue and the atmosphere so that the EMD can receive it.

A first IMD telemetry antenna element is supported to extend in a first direction along a first minor side of a substantially rectilinear, conductive IMD housing, and a second antenna element is supported to extend in a second direction along a second minor side of the substantially rectilinear, conductive IMD housing. The first and second antenna elements are supported to extend apart at substantially 90° to one another, i.e., substantially orthogonally, in substantially a common plane to optimize UT transmission and DT reception by at least one of the first and second antenna elements depending upon the spatial orientation of the IMD antenna elements to similar EMD antenna elements.

The EMD, typically a programmer, is also provided with orthogonally disposed first and second antenna elements of the types disclosed in the above-referenced commonly assigned '317 patent, for example. The first and second orthogonally disposed telemetry antenna elements of the respective IMD and EMD telemetry antennas thus each exhibit two orthogonal linear polarizations that emulate desirable circular polarization characteristics. Moreover, as described below, the IMD telemetry antenna is tuned to minimize power losses in body tissue for UHF transmissions at about a 403 MHz RF carrier frequency.

Figure 10:
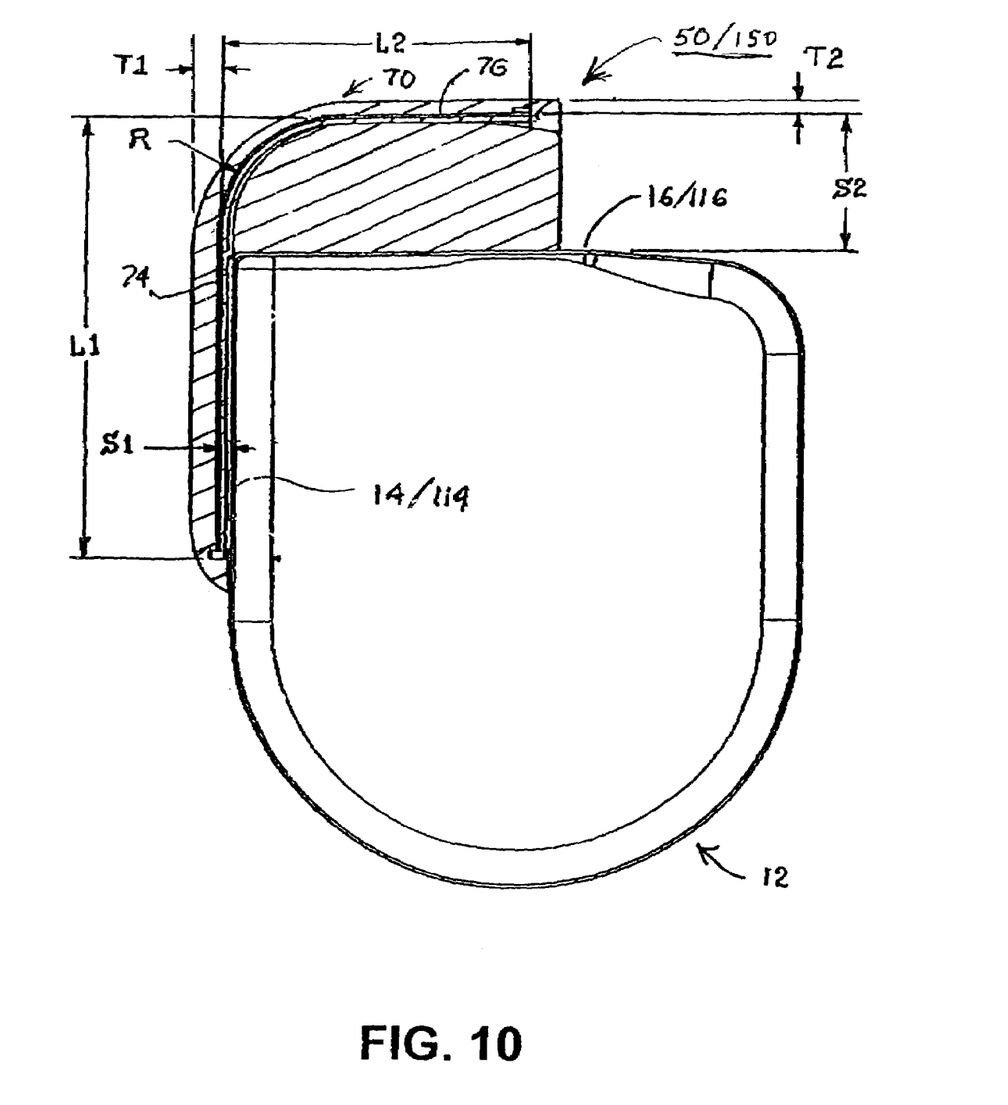
FIG. 10 is a schematic dimensional illustration of the orthogonal disposition of the first and second telemetry elements of the first and second embodiments with respect to the ICD IPG housings.

Turning to the first preferred IMD embodiment illustrated in FIGS. 1–6 and in reference to FIG. 10, an ICD IPG 10 comprises a hermetically sealed housing 12 and a connector header 50. A set of ICD leads having cardioversion/defibrillation electrodes and pace/sense electrodes disposed in operative relation to a patient's heart are adapted to be coupled to the connector header 50 in a manner well known in the art. The ICD IPG 10 is adapted to be implanted subcutaneously in the body of a patient such that the first and second orthogonally disposed IMD telemetry antenna elements are encased within body tissue and fluids including epidermal layers, subcutaneous fat layers and/or muscle layers.

Figure 6:
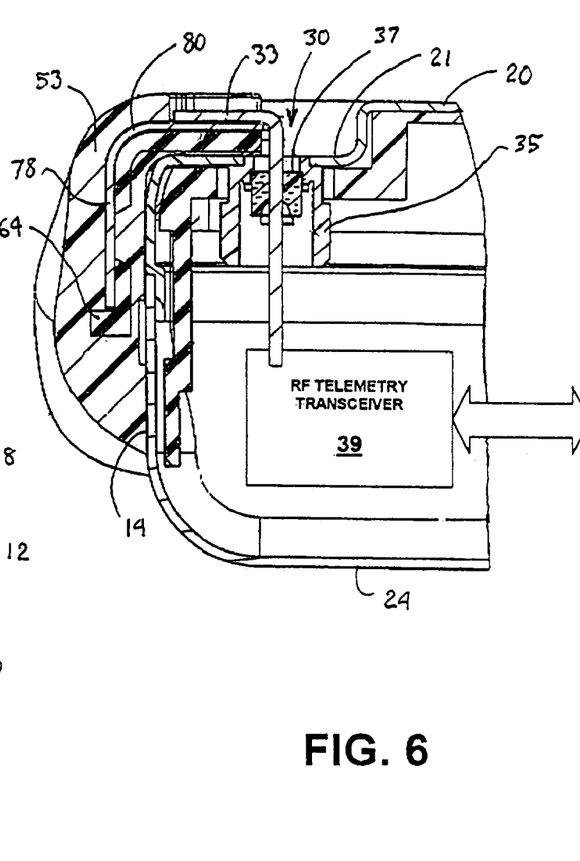
FIG. 6 is an enlarged cross-section view taken along lines 6—6 in FIG. 1 depicting the attachment of the external end of the antenna feedthrough pin to a welding tab of the telemetry antenna wire strip and the internal end of the antenna feedthrough pin to schematically depicted RF transceiver circuitry of the ICD IPG.
Figure 7:
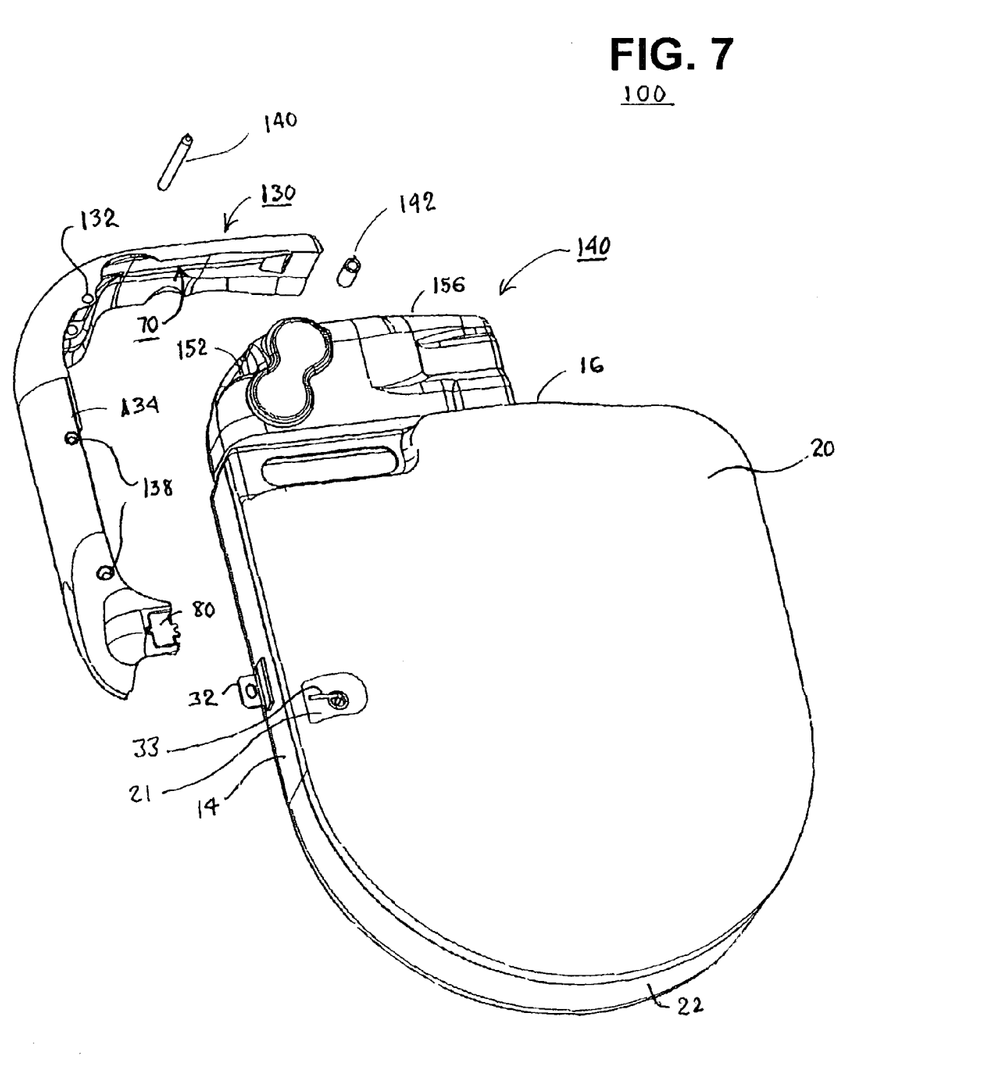
FIG. 7 is a perspective exploded front view of a second embodiment of the invention affixing an IMD telemetry antenna within an adaptor connector module to an ICD IPG having a conventionally formed IPG connector header in accordance with a second embodiment of the invention.

The hermetically sealed housing 12 is generally prismatic or rectilinear having substantially planar major sides 20 and 24 joined by perimeter sides comprising substantially straight first minor side 14, second minor side 16, and third minor side 18 and a curvilinear fourth minor side 22. The first and second minor sides 14 and 16 are joined at a mutual corner or side junction 15. The hermetically sealed housing 12 is typically formed of a thin-walled biocompatible metal, e.g., titanium, shaped half sections that are laser seam welded together in a seam extending around the minor sides 14, 16, 18 and 22. A telemetry recess 21 is formed into the planar major side 20 adjacent first minor side 14 that includes a telemetry feedthrough hole that an IPG telemetry antenna feedthrough 30 described further below with reference to FIG. 6 is welded into. A connector recess 23 is formed into the planar major side 20 adjacent to second minor side 16 that includes an elongated feedthrough hole that accommodates a single, elongated, feedthrough 40 supporting a plurality of feedthrough pins 41 (shown only in all figures for convenience). A connector tab 32 extends away from the first housing side 14, and connector tabs 32, 34, 36 extend away from the second housing side 16.

The hermetically sealed IPG housing 12 is manufactured as an assembly or attachment with the separately fabricated IPG connector header 50. One or more battery, high voltage output capacitor, and IC package, and other components are assembled in spacers and disposed within the an interior cavity of housing 12 prior to seam welding of the housing halves as shown, for example, in commonly assigned U.S. patent application Ser. No. 10/132,781 filed Apr. 25, 2002, by Ries et. al., for ELECTRICALLY INSULATED COMPONENT SUB-ASSEMBLIES OF IMPLANTABLE MEDICAL DEVICES. In the manufacturing process, electrical connections are made between IC connector pads or terminals with the inner ends of the connector header feedthrough pins. An electrical connection is also made between the inner end of the antenna feedthrough pin of antenna feedthrough 30 and the IPG telemetry transceiver circuit as described further below in reference to FIG. 6.

Figure 1:
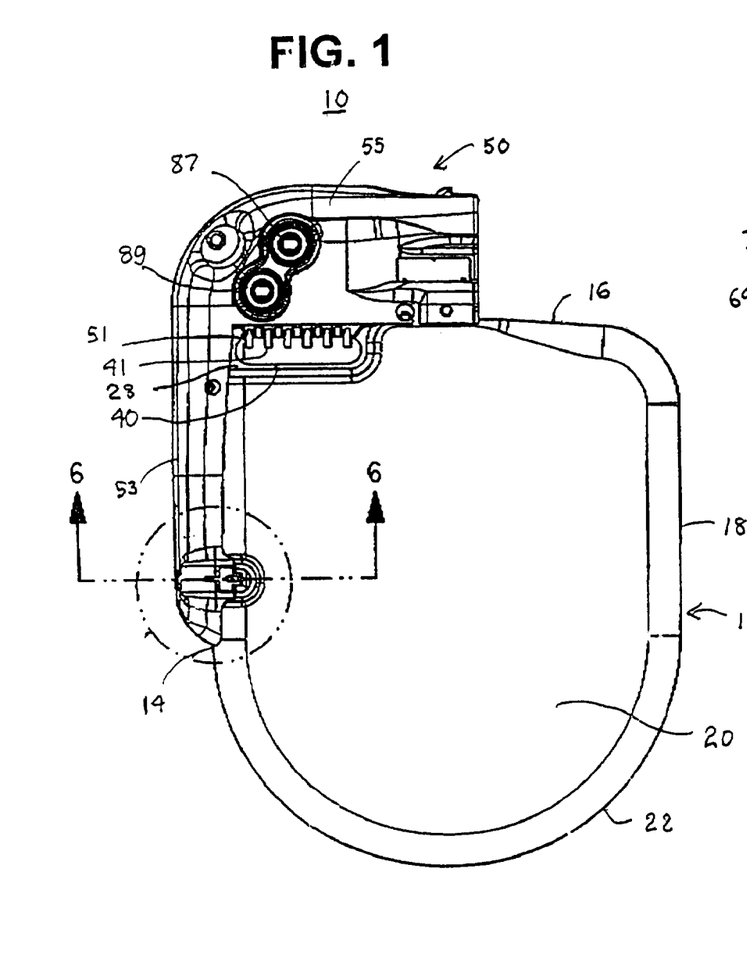
FIG. 1 is a plan view of a first embodiment of an ICD IPG fabricated with an elongated IMD antenna within the IPG connector header in accordance with a first embodiment of the invention.
Figure 2:
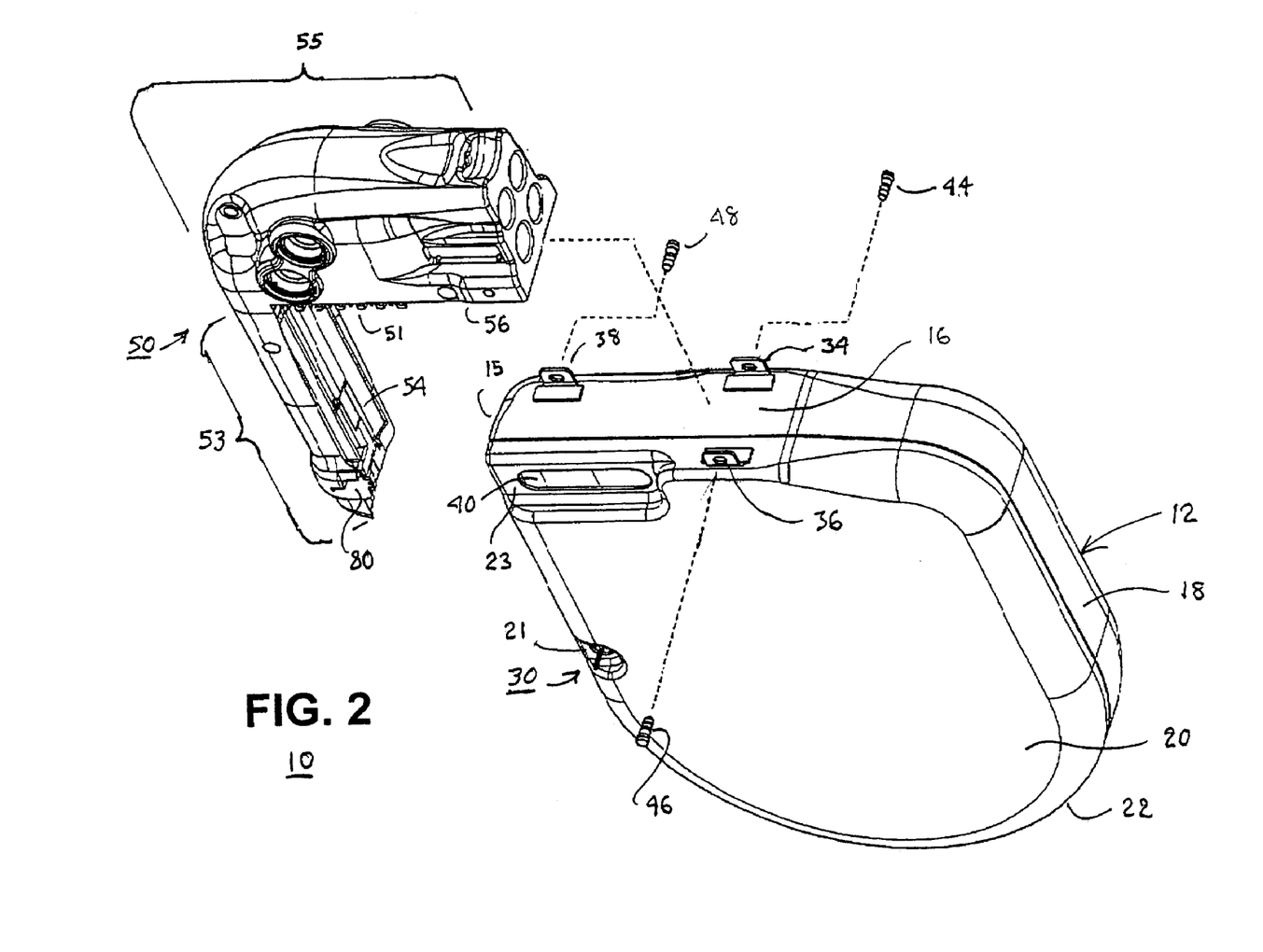
FIG. 2 is an exploded front perspective view of the ICD IPG of FIG. 1 depicting the IPG connector header disposed in relation to the ICD IPG housing.
Figure 3:
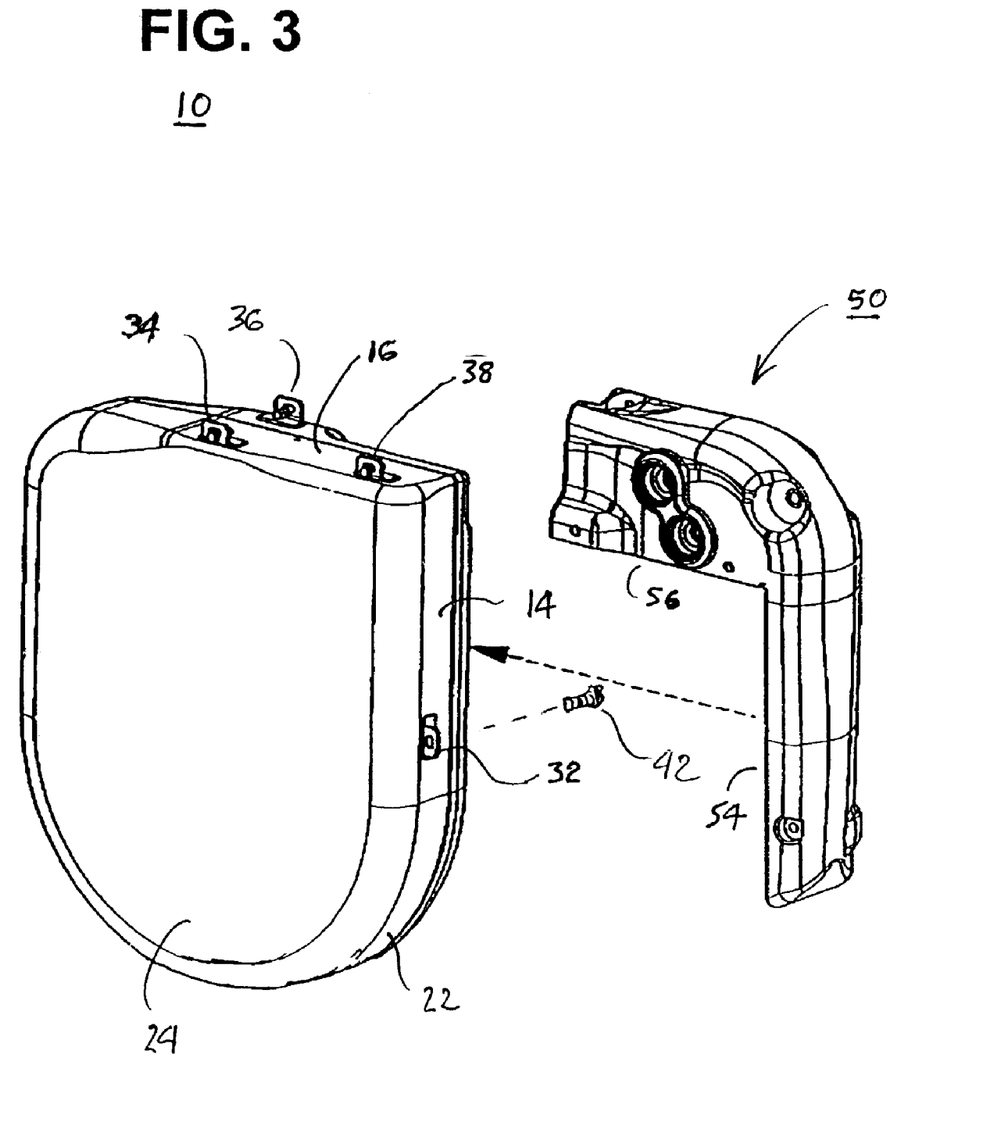
FIG. 3 is an exploded rear perspective view of the ICD IPG of FIG. 1 depicting the IPG connector header disposed in relation to the ICD IPG housing.

The IPG connector header 50 is also formed as a separate assembly comprising a first header segment 53 and a second header segment 55 having substantially contiguous header segment sides 54 and 56, respectively, that are shaped to fit against the contiguous first and second minor sides 14 and 16 and to receive connector tabs 32, 34, 36 and 38. The IPG connector header 50 is mechanically fixed to the first and second minor sides 14 and 16 by use of pins or screws 42, 44, 46, and 48 that fit through aligned holes in IPG connector header 50 and the respective connector tabs 32, 34, 36, and 38. The IPG connector header 50 is also formed with an array of connector header electrical pads 51 that fit into the telemetry recess 21. As shown in FIG. 1, each of the connector feedthrough pins 41 are bent over and welded to a respective one of the electrical pads 51. After testing, the telemetry recess 21 is filled with biocompatible medical adhesive or epoxy to cover and electrically insulate the welded together connector feedthrough pins 41 and electrical pads 51 from body fluids.

Figure 4:
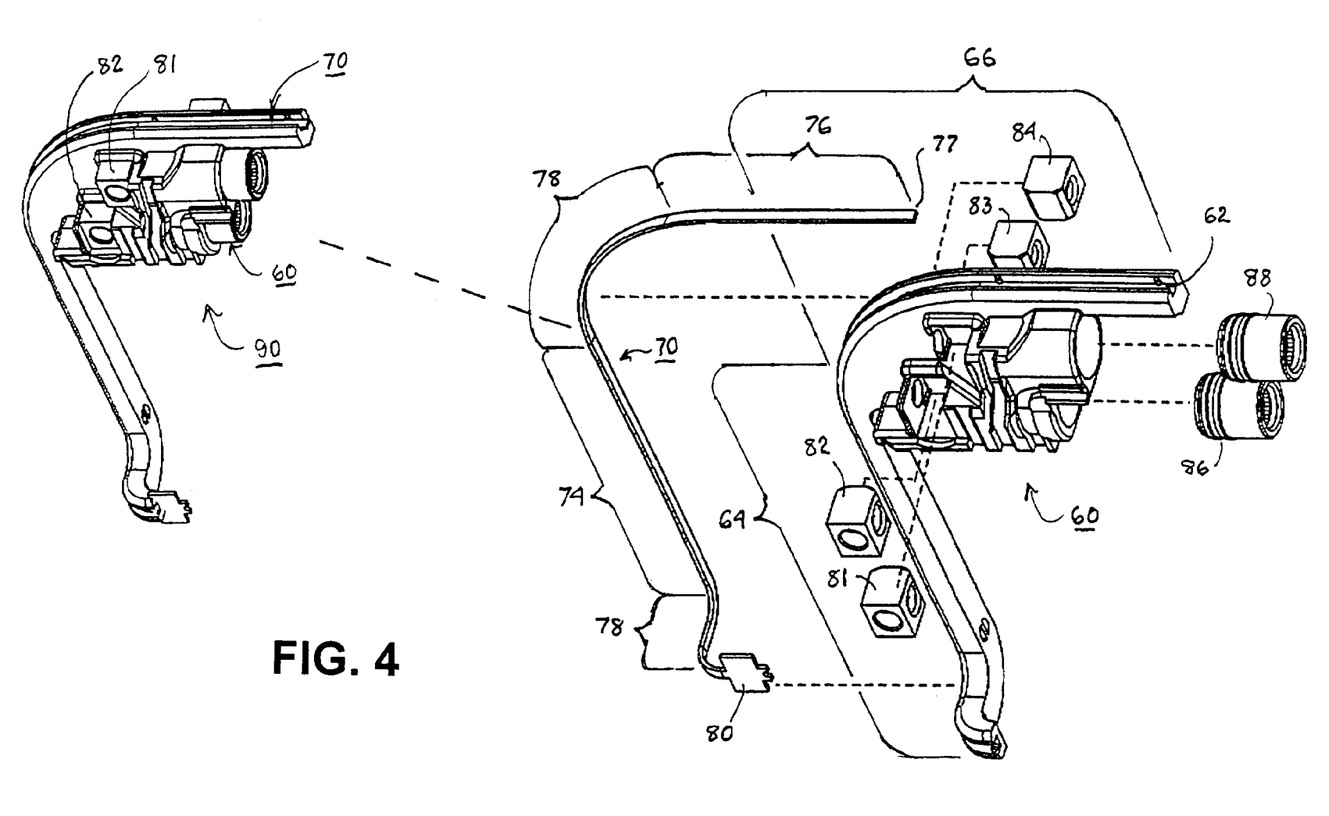
FIG. 4 is an exploded perspective view of an undermold supporting the elongated IMD telemetry antenna as well as connector blocks, and connector rings employed in an IPG connector header having four connector bores accepting two unipolar and two bipolar lead connector assemblies.

Referring to FIG. 4, the elongated IMD telemetry antenna 70 comprises a wire strip bent at substantially 90° bend 72 into orthogonally extending first and second telemetry antenna elements 74 and 76. The second telemetry antenna element 76 extends from the substantially 90° bend 72 to a wire strip free end 77. The first telemetry antenna element 74 extends from the substantially 90° bend 72 to a lateral wire strip bend 78 over to a wire strip fixed end at connector pad 80.

In this preferred embodiment, the IPG connector header 50, including the first and second header segments 53 and 55, is formed of an integral undermolded frame or "undermold" 60 formed of polymer, e.g., polyurethane, that supports the wire strip IMD telemetry antenna 70 and the depicted connector header components. A polymeric overmold 57 is molded over the sub-assembly of the IPG telemetry antenna and the connector header components, thereby sealing the sub-assembled components and providing a radome over the wire strip IPG telemetry antenna. The IPG connector header 50 is then assembled to the IPG hermetically sealed housing 12, and the IPG telemetry antenna fixed end is electrically connected to the IPG telemetry transceiver.

More particularly, the undermold 60 is molded having first and second undermold segments 64 and 66. An outer channel 62 of the undermold 60 extends through the first and second undermold segments 64 and 66 and is shaped to the shape of the wire strip IPG telemetry antenna 70 as shown in FIG. 4. The first undermold segment 64 is also shaped to define IPG connector bores and to support header connector elements 81, 82, 83, 84, 86 and 88. The header connector elements 81, 82, 83, 84 receive the proximal connector pins of cardiac leads inserted into the connector bores and comprise conventional setscrews accessed through penetrable silicone rubber setscrew grommets, e.g., grommets 87 and 89 of FIG. 1, to tighten the lead connector pins in place in a manner well known in the art. The tubular connector rings 86 and 88 include inwardly extending resilient force beams that bear against connector rings of bipolar lead connector assemblies of cardiac leads inserted into connector bores in a manner well known in the art. The undermold 60 and wire strip IPG telemetry antenna 70 are assembled together to form the undermold sub-assembly 90 depicted in FIGS. 4 and 5. It will be understood that the terminals of conductors of a conductor assembly (not shown) are also welded to the connector elements 81, 82, 83, 84, 56 and 88 and terminate in the connector pad array 51 depicted in FIG. 1.

A polymeric overmold 57 is then molded from a suitable polymer, e.g., a medical grade polyurethane, over the undermold sub-assembly 90. The overmold 57 defines various features of the IPG connector header 50 that are not important to the practice of the present invention, including the outer contours, the connector bore openings, suture holes, and attachment bore openings, setscrew access openings, etc. In this regard, it should be noted that the overmold 57 is molded to define an inner bipolar connector bore aligned with the connector block 82 and connector ring 86 for receiving a first bipolar lead connector pin and ring. Similarly, the overmold 57 is molded to define an outer bipolar connector bore aligned with the connector block 81 and connector ring 88 for receiving a second bipolar lead connector pin and ring. The overmold 57 is also molded to define inner and outer unipolar connector bores that are aligned with the connector blocks 83 and 84, respectively, to receive first and second unipolar lead connector pins. The number, types and particular configurations of the lead connector elements and connector bores are not important to the practice of the present invention.

Figure 5:
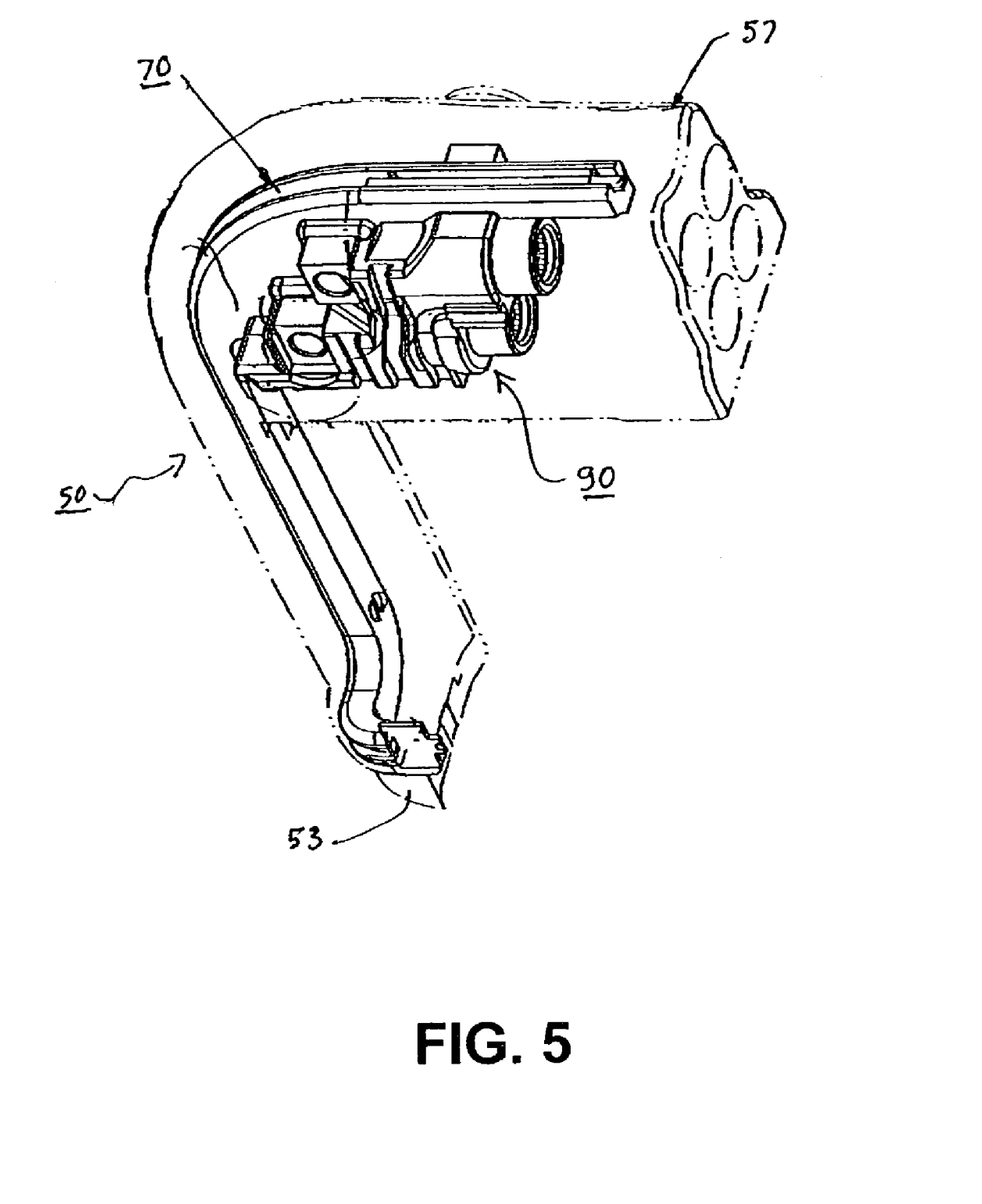
FIG. 5 is a perspective view of an overmold molded over the assembly of the undermold, connector blocks, sealing rings, and the elongated IMD telemetry antenna of FIG. 4.

More importantly, overmold 57 and the undermold 60 do define the shapes of the header sides 54 and 56 that match the shapes of the housing minor sides 14 and 16, respectively. The overmold 57 also seals the IPG telemetry antenna 70 within the undermold channel 62, except for the outer surface of the antenna connector pad 80, which is left exposed as shown in FIG. 5. The overmold 57 thereby seals the assembled components of undermold sub-assembly 90, and provides a radome over the first and second, wire strip, antenna elements 74 and 76 of IPG antenna 70 and otherwise electrically insulates the telemetry antenna 70 from body tissue and fluid. The connector header pad array 51 is also left exposed by the overmold 57 to enable attachment to the connector feedthrough pins 41 as described above. As noted above, the attachment of the IPG connector header 50 to the hermetically sealed housing 12 is effected using the pins or screws 42, 44, 46, and 48. Medical adhesive or epoxy is also typically injected through fill holes in the overmold 57 into interior spaces and gaps to seal the assembly and enhance adhesion of the IPG connector header to the first and second minor sides 14 and 16.

As shown in FIG. 6, the feedthrough 30 comprises a ferrule 35 supporting a non-conductive glass or ceramic (e.g., alumina) annular insulator, that in turn supports and electrically isolates the feedthrough pin 33 from the ferrule 35. During assembly of the hermetically sealed housing 12, the ferrule 35 is welded to a feedthrough opening or hole through the housing major side 20 within the telemetry recess 21. The RF telemetry transceiver 39 (depicted schematically in FIG. 6) is electrically connected to the inner end of the antenna feedthrough pin 33. The connection of the RF telemetry transceiver 39 to the inner end of the antenna feedthrough pin 33 can be made in a variety of ways as by welding the inner end of the antenna feedthrough pin 33 to a substrate pad or clipping the inner end of the antenna feedthrough pin 33 to a cable or flex wire connector extending to a substrate pad or connector. The inner end of the antenna feedthrough pin 33 is electrically coupled to RF transceiver circuitry 39 disposed in close proximity thereto, in a manner that advantageously facilitates impedance matching and reduces losses The electrical connection is made between the wire strip antenna fixed end at antenna connector pad 80 with the outer end of the antenna feedthrough pin 33 of antenna feedthrough 30 after the antenna connector pad 80 is slipped laterally into the telemetry recess 21 such that the outer extending portion of the feedthrough pin 33 fits into a notch in the leading edge of the antenna connector pad 80 during assembly of the IPG connector header 50 with the hermetically sealed housing 12. As shown in FIG. 6, the outer extending portion of the feedthrough pin 33 is bent over the exposed outer surface of the antenna connector pad 80 and laser welded thereto. The feedthrough pin outer end and the wire strip fixed end are laser welded together in a low profile weld within the telemetry recess 21 formed in the housing major side 20. After testing, the telemetry recess 21 is filled with medical adhesive or epoxy to cover and electrically insulate the bent over, outer extending portion of the feedthrough pin 33 and the exposed outer surface of the antenna connector pad 80.

Thus, the IPG telemetry antenna 70 comprising the orthogonally disposed first and second antenna elements 74 and 76 is enclosed within and supported by the integrally formed connector header 50. The wire strip telemetry antenna 70 is attached to the outer end of the antenna feedthrough pin 33 that extends through the wall of the hermetically sealed housing 12 at a distance from the second header segment 55, thereby not interfering with the mechanical and electrical connections and components therein and allowing the wire strip antenna free end 77 to be displaced from the second minor side 16.

In a second embodiment of the invention, an ICD IPG 100 depicted in FIGS. 6–9 comprises the same hermetically sealed housing 12 as the first embodiment of FIGS. 1–6 providing the telemetry antenna feedthrough 30 mounted to the housing side 20 within telemetry recess 21 and electrically connected to the IPG telemetry transceiver circuit 39 as depicted in FIG. 6. However, a conventional, pre-formed, IPG connector header 140 is separately fabricated and affixed to the pre-formed hermetically sealed housing 12 following conventional fabrication techniques. The pre-formed IPG connector header 140 depicted in FIG. 7 that is already attached to the second minor side 16 conforms in configuration, internal components and assembly to the second minor side 16 as described above with respect to the second header segment 56 of IPG connector header 50. Details, e.g., the connector feedthrough pins 41 and tabs 51 that would be within recess 23 and the penetrable setscrew grommets, are not shown in all of FIGS. 7–9 to simplify the illustration.

Figure 8:
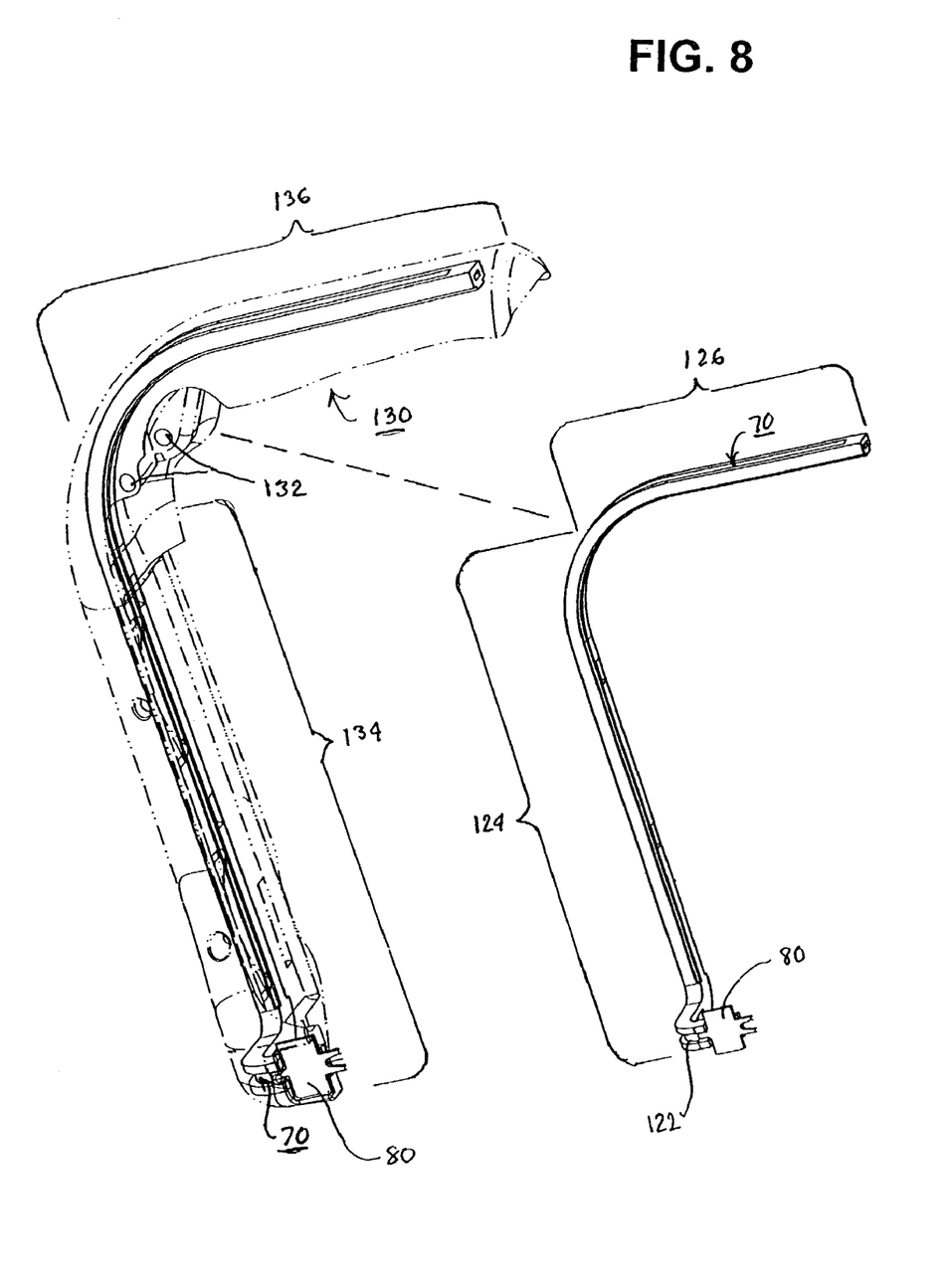
FIG. 8 is an exploded view of the wire strip in relation to the adaptor connector module of the second embodiment of the invention.
Figure 9:
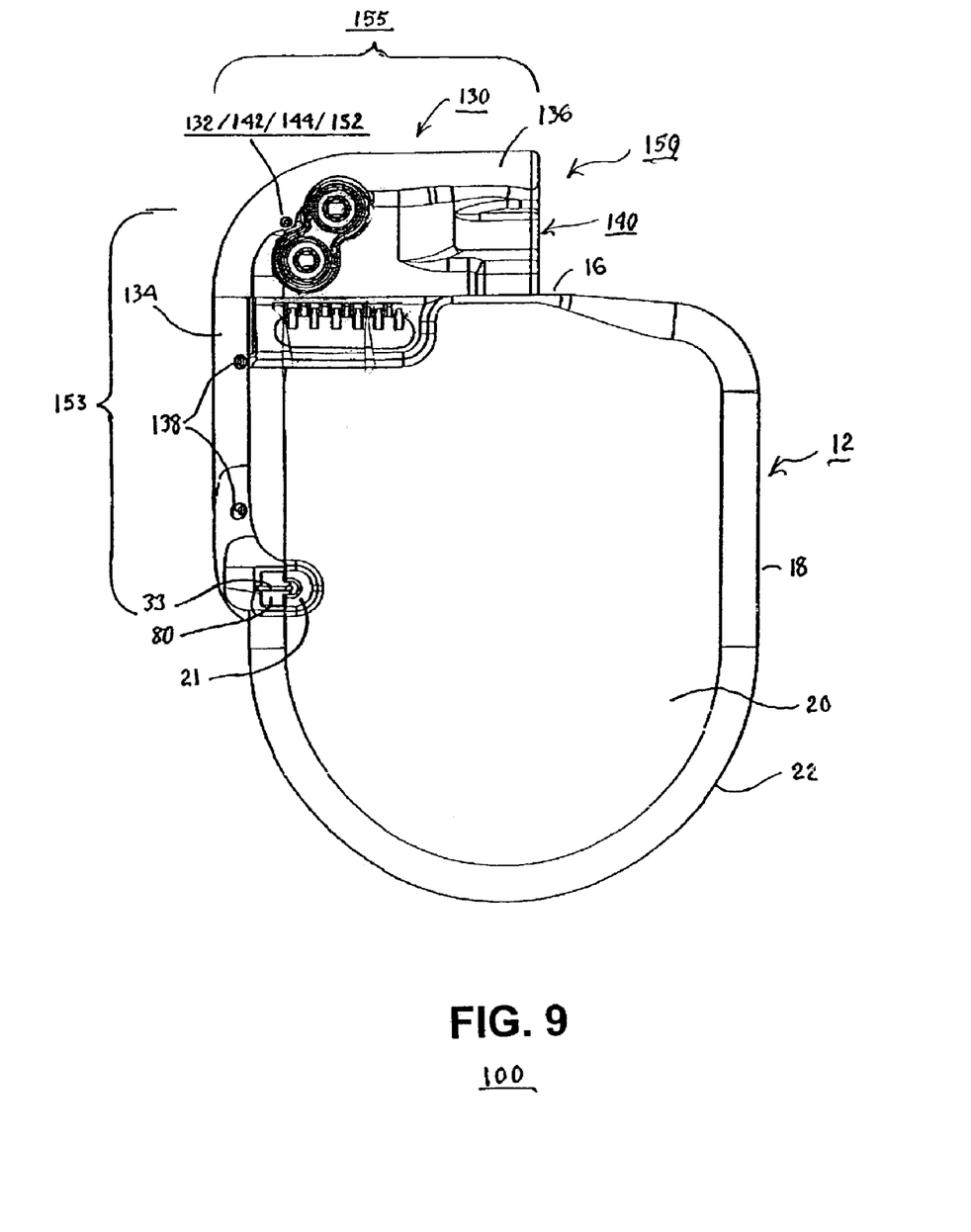
FIG. 9 is a plan view of the wire strip and adaptor connector module assembled to the ICD IPG in accordance with the second embodiment of the present invention.

In this embodiment, as illustrated in FIG. 8, the telemetry antenna 70 is supported within a conforming channel 122 of a further undermold 120, and the assembly of undermold 120 and IPG telemetry antenna 70 is embedded within a further overmolded antenna connector module 130. The further undermold 120 comprises a first undermold segment 124 supporting the first telemetry antenna element 74 and a second undermold segment 126 supporting the second telemetry antenna segment 76. The antenna connector module 130 similarly comprises a first overmolded module segment 134 encasing and providing a radome for the first telemetry antenna element 74 and a second overmolded module segment 136 encasing and providing a radome for the second telemetry antenna segment 76.

The first and second overmolded module segments 134 and 136 are shaped and dimensioned to bear against the first minor side 14 and the outer header surface 156 of the pre-formed IPG connector header 140, respectively. The antenna connector module 130 is formed with a bore 132 that is aligned with a suture hole 152 of the connector bore when the antenna connector module 130 is disposed against the first minor side 14 and the header outer surface 156. An adaptor sleeve 142 is fitted into the suture hole 152, and an adaptor pin 144 is fitted through the aligned bore 132 and adaptor sleeve 12 fitted into the suture hole 152 to fix the antenna connector module 130 to the pre-formed IPG connector header 140. In addition, the adaptor connector module 130 is shaped with an intersecting slot and bore (not shown) that receives the connector tab 32 and titanium pin 42 (shown in FIG. 2) of the hermetically sealed housing 12. Moreover, medical adhesive or epoxy can be injected through a plurality of adhesive ports 138 into the gaps between the first and second overmolded module segments 134 and 136 and the first minor side 14 and the outer surface 156 of the pre-formed IPG connector header 140, respectively.

Again, the antenna connector pad 80 is slipped laterally into the telemetry recess 21 such that the outer extending portion of the feedthrough pin 33 fits into a notch in the leading edge of the antenna connector pad 80 during assembly of the IPG connector header 50 with the hermetically sealed housing 12 as shown in FIG. 6. The outer extending portion of the feedthrough pin 33 is bent over the exposed outer surface of the antenna connector pad 80 and welded thereto. After testing, the telemetry recess 21 is filled with medical adhesive or epoxy to cover and electrically insulate the bent over, outer extending portion of the feedthrough pin 33 and the exposed outer surface of the antenna connector pad 80. Upon completion of the assembly, a composite IPG connector header 150 is formed effectively comprising first and second header segments 153 and 155, respectively.

FIG. 10 schematically illustrates the relative dimensions and spacings of the first and second antenna elements 74 and 76 within the first and second header segments 53 and 54, respectively, of the integral connector header 50 and within the first and second header segments 153 and 154, respectively, of the composite connector header 150.

The first antenna element 74 has a first length L1 within the first header segment 53, 153 and is supported to extend substantially parallel to and at a first side spacing S1 from a first minor side 14 of the hermetically sealed housing 12. The length dimension L1 is related to the available length of the first minor side 14. Similarly, the second antenna element 76 has a second length L2 within the second header segment 55, 155 and is supported to extend substantially parallel to and at a second side spacing S2 from the second minor side 16. The second side spacing S2 is dictated in part by the dimensions of the connector elements.

The dielectric overmold material of the overmold between the first antenna element 74 and the outer surface of the first header segment 53, 153 has a first radome thickness T1 that provides a radome over the first antenna element 74. The dielectric overmold material of the overmold between the second antenna element 76 and the outer surface of the second header segment 55, 155 has a second radome thickness T2 that provides a radome over the second antenna element 76. The radome thicknesses T1 and T2 can be theoretically calculated and empirically confirmed or adjusted so that the antenna 70 is tuned for optimal reception and transmission at the nominal 403 MHz carrier frequency operating within body tissue over the specified range.

In one example, the IMD telemetry antenna 70 is constructed as a flat titanium wire that is 0.010 inches thick, 0.025 inches wide, and 3.04 inches long overall. The side spacing S1 can be set to between 0.040 and 0.050 inches, for example, and the side spacing S2 can be set to between 0.480 and 0.500 inches, for example. The radome thicknesses T1 and T2 can be set to about 0.020 inches. Reliable telemetry transmission and reception over a distance of at least two meters at the nominal 403 MHz carrier frequency operating within air and body tissue between the IMD telemetry antenna 70 and an EMD telemetry antenna is partly provided by these IMD telemetry antenna preferred embodiments of the invention.

This antenna design meets the system requirements for the two meter minimum range and provides adequate gain, gain pattern, bandwidth, and tunability using one or more reactive element for different possible environments before and after implanting of the IMD, particularly for implantation in muscle layers. The polarization of the IMD telemetry antenna 70 becomes circular in muscle and close to linear in fat. The polarization depends on the environment that the IMD is located in. The polarization is close to linear when the IMD is in an environment of a relatively low permittivity and low conductivity, e.g., air or body fat. The polarization is ellipsoidal or circular in muscle because the permittivity and conductivity of muscle is much higher, which results in a shorter wavelength than the wavelength would be in air. This is especially the case for the main lobe of the gain pattern.

A wave exhibiting the ellipsoidal or circular polarization is advantageous in the present invention because the programmer or other EMD that communicates with the IMD also has two orthogonally disposed antenna elements providing two respective orthogonal linear polarizations. As noted above, when the IMD is implanted within muscle, then the signal losses will be higher due to the higher conductivity of the muscle tissue. The circular polarization improves the communication in this case. This, in addition to the fact that the IMD telemetry antenna is tuned for implantation in muscle enables achievement of the two meter minimum range for the worst case scenario.

Although the preferred embodiments describe the incorporation of the telemetry antenna 70 within a connector header, it will be understood that the present invention may be incorporated into implantable monitors of the type having a non-conductive header that supports one or more sense electrode or other sensors rather than connector components for making electrical connection with electrical medical leads. Consequently, the term "header" is intended to encompass "connector headers" as well as such monitor headers or other IMD headers that the present invention can be advantageously incorporated with.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

What is claimed is:

1. An implantable medical device of the type adapted to provide a therapy to the body and/or to monitor a physiologic condition and to communicate with an external medical device by telemetry transmissions comprising:
    a hermetically sealed housing enclosing a telemetry transceiver, the enclosure housing having first and second major sides joined by minor sides separating the major sides apart, at least first and second minor sides joined at a minor side junction and extending substantially orthogonally away from the side junction;
    a telemetry antenna feedthrough attached to the hermetically sealed housing at a distance along the first minor side from the side junction having a telemetry feedthrough pin coupled at a feedthrough pin inner end to the telemetry transceiver and having a feedthrough pin outer end;
    a header formed of dielectric material comprising a first header segment attached to and extending along the first housing side from a point adjacent to the telemetry antenna feedthrough to the side junction and a second header segment enclosing header components attached to and extending along the second minor side from the side junction; and
    an elongated telemetry antenna extending from a telemetry antenna free end to a telemetry antenna fixed end that is attached to the telemetry feedthrough pin outer end, the telemetry antenna comprising a first antenna element supported by the first header segment to extend along the first minor side at a first spacing from the first minor side and a second antenna element supported by the second header segment to extend along the second minor side at a second spacing from the second minor side to the telemetry antenna free end.

2. The implantable medical device of claim 1, wherein the first and second telemetry antenna elements are supported by the respective first and second header segments to extend substantially orthogonally away from the side junction in substantially a common plane.

3. The implantable medical device of claim 2, wherein the telemetry antenna is embedded within the dielectric material of the header and the first and second header segments have first and second header segment outer surfaces, respectively, adapted to contact body tissue upon implantation, whereby the dielectric material overlying the first and second antenna elements functions as a radome.

4. The implantable medical device of claim 3, wherein:
    the first antenna element has a first length and is supported to extend at a first side spacing from the first minor side and to extend at substantially a first radome thickness from the first header segment outer surface; and
    the second antenna element has a second length and is supported to extend at a second side spacing from the second minor side and to extend at substantially a second radome thickness from the second header segment outer surface,
    whereby the first and second antenna elements are tuned for optimal RF telemetry reception and transmission through body tissue and air.

5. The implantable medical device of claim 4, wherein the second header segment encloses connector components for coupling with electrical medical leads.

6. The implantable medical device of claim 5, wherein the connector components for coupling with electrical medical leads are disposed in the second side spacing between the second antenna element and the second minor side.

7. The implantable medical device of claim 6, wherein the header comprises:
    an undermold of polymeric material extending through the first and second header segments supporting the connector components and the telemetry antenna; and
    an overmold molded over the undermold and the telemetry antenna.

8. The implantable medical device of claim 6, wherein:
    the second header segment comprises a pre-formed header fitted to the second minor side of the hermetically sealed housing having a pre-formed header outer surface spaced from the second minor side; and
    the first and second header segments further comprise an antenna connector module supporting the telemetry antenna and having first and second module segments, the first module segment attached with the first minor side and the second module segment attached with the pre-formed header outer surface.

9. The implantable medical device of claim 2, wherein:
    the first antenna element has a first length and is supported to extend at a first side spacing from the first minor side and to extend at substantially a first radome thickness from a first header segment outer surface; and
    the second antenna element has a second length and is supported to extend at a second side spacing from the second minor side and to extend at substantially a second radome thickness from a second header segment outer surface, whereby the first and second antenna elements are tuned for optimal RF telemetry reception and transmission through body tissue and air.

10. The implantable medical device of claim 2, wherein the second header segment encloses connector components for coupling with electrical medical leads.

11. The implantable medical device of claim 10, wherein the connector components for coupling with electrical medical leads are disposed in the second side spacing between the second antenna element and the second minor side.

12. The implantable medical device of claim 11, wherein the header comprises:
an undermold of polymeric material extending through the first and second header segments supporting the connector components and the telemetry antenna; and
an overmold molded over the undermold and the telemetry antenna.

13. The implantable medical device of claim 2, wherein:
the second header segment comprises a pre-formed header fitted to the second minor side of the hermetically sealed housing having a pre-formed header outer surface spaced from the second minor side; and
the first and second header segments further comprise an antenna connector module supporting the telemetry antenna and having first and second module segments, the first module segment attached with the first minor side and the second module segment attached with the pre-formed header outer surface.

14. The implantable medical device of claim 1, wherein:
the second header segment comprises a pre-formed header fitted to the second minor side of the hermetically sealed housing having a pre-formed header outer surface spaced from the second minor side; and
the first and second header segments further comprise an antenna connector module supporting the telemetry antenna and having first and second module segments, the first module segment attached with the first minor side and the second module segment attached with the pre-formed header outer surface.

15. The implantable medical device of claim 1, wherein:
the first antenna element has a first length and is supported to extend at a first side spacing from the first minor side and to extend at substantially a first radome thickness from a first header segment outer surface; and
the second antenna element has a second length and is supported to extend at a second side spacing from the second minor side and to extend at substantially a second radome thickness from a second header segment outer surface,
whereby the first and second antenna elements are tuned for optimal RF telemetry reception and transmission through body tissue and air.

16. The implantable medical device of claim 1, wherein the second header segment encloses connector components for coupling with electrical medical leads.

17. The implantable medical device of claim 16, wherein the connector components for coupling with electrical medical leads are disposed between the second antenna element and the second minor side.

18. The implantable medical device of claim 17, wherein the header comprises:
an undermold of polymeric material extending through the first and second header segments supporting the connector components and the telemetry antenna; and
an overmold molded over the undermold and the telemetry antenna.

19. The implantable medical device of claim 1, wherein the telemetry antenna feedthrough is attached to a feedthrough opening extending through the first major side adjacent to the first minor side, and the telemetry antenna fixed end extends to the telemetry feedthrough pin outer end.

20. The implantable medical device of claim 1, wherein:
the first major side is formed with a telemetry recess and feedthrough opening adjacent to the first minor side;
the telemetry antenna feedthrough is attached to the feedthrough opening extending through the first major side adjacent to the first minor side;
the telemetry antenna fixed end comprises an antenna pad extending into the telemetry recess;
the telemetry feedthrough pin outer end is attached to the antenna pad within the telemetry recess; and
the telemetry recess, antenna pad, and the telemetry feedthrough pin outer end are covered with a biocompatible electrically insulating material.

21. An implantable medical device of the type adapted to provide a therapy to the body and/or to monitor a physiologic condition and to communicate with an external medical device by telemetry transmissions comprising:
a hermetically sealed housing enclosing a telemetry transceiver, the enclosure housing having first and second major sides joined by minor sides separating the major sides apart, at least first and second minor sides joined at a side junction and extending substantially orthogonally away from the side junction;
a telemetry antenna feedthrough attached to the hermetically sealed housing at a distance along the first minor side from the side junction having a telemetry feedthrough pin attached at a feedthrough pin inner end to the telemetry transceiver and a feedthrough pin outer end;
an elongated telemetry antenna extending from a telemetry antenna fixed end to a telemetry antenna free end and having first and second antenna elements;
attaching means for attaching the telemetry antenna fixed end to the feedthrough pin outer end; and
supporting means for supporting the first antenna element along the first minor side at a first side spacing from the first minor side and the second antenna element extending along the second minor side at a second side spacing from the second minor side, the first and second antenna elements extending substantially orthogonally away from the side junction in substantially a common plane.

22. The implantable medical device of claim 20, wherein:
the first antenna element has a first length and is supported by the supporting means to extend at the first side spacing from the first minor side; and
the second antenna element has a second length and is supported by the supporting means to extend at the second side spacing from the second minor side.

23. The implantable medical device of claim 22, wherein the supporting means is formed of a dielectric material that encloses the first and second antenna elements and forms a radome overlying the first and second antenna elements, whereby the first and second antenna elements are tuned for optimal RF telemetry reception and transmission through body tissue and air.

24. The implantable medical device of claim 21, wherein the telemetry antenna feedthrough is attached to a feedthrough opening extending through the first major side adjacent to the first minor side, and the telemetry antenna fixed end extends to the telemetry feedthrough pin outer end and is attached thereto.

25. The implantable medical device of claim 21, wherein:
- the first major side is formed with a telemetry recess and feedthrough opening adjacent to the first minor side;
- the telemetry antenna feedthrough is attached to the feedthrough opening extending through the first major side adjacent to the first minor side;
- the telemetry antenna fixed end comprises an antenna pad extending into the telemetry recess;
- the telemetry feedthrough pin outer end is attached to the antenna pad within the telemetry recess; and
- the telemetry recess, antenna pad, and the telemetry feedthrough pin outer end are covered with a biocompatible electrically insulating material.

26. A method of fabricating an implantable medical device of the type adapted to provide a therapy to the body and/or to monitor a physiologic condition and to communicate with an external medical device by telemetry transmissions comprising:
- forming a hermetically sealed housing enclosing a telemetry transceiver, the enclosure housing having first and second major sides joined by minor sides separating the major sides apart, at least first and second minor sides joined at a side junction and extending substantially orthogonally away from the side junction;
- attaching a telemetry antenna feedthrough to the hermetically sealed housing at a distance along the first minor side from the side junction, the telemetry antenna feedthrough having a telemetry feedthrough pin attached at a feedthrough pin inner end to the telemetry transceiver and a feedthrough pin outer end;
- forming an elongated telemetry antenna extending from a telemetry antenna fixed end to a telemetry antenna free end and having first and second antenna elements;
- supporting the first antenna element along the first minor side at a first spacing from the first minor side and the second antenna element extending along the second minor side at a second spacing from the second minor side, the first and second antenna elements extending substantially orthogonally away from the side junction in substantially a common plane.

* * * * *